(12) United States Patent
Truong et al.

(10) Patent No.: US 6,605,436 B1
(45) Date of Patent: Aug. 12, 2003

(54) METHOD AND KIT FOR DETECTING INTRACHROMOSOME IMBALANCE IN INTERPHASE NUCLEI AND THEIR APPLICATIONS

(75) Inventors: Khuong Truong, Paris (FR); Bernard Malfoy, Paris (FR); Claire Bourgeois, Paris (FR); Philippe Vielh, Paris (FR); Marie-Noëlle Guilly, Paris (FR); Bernard Dutrillaux, Paris (FR)

(73) Assignees: Commissariat a l'Energie Atomique, Paris (FR); Centre National de la Recherche Scientifique, Paris (FR); Institut Curie, Paris (FR)

( * ) Notice: Subject to any disclaimer, the term of this patent is extended or adjusted under 35 U.S.C. 154(b) by 0 days.

(21) Appl. No.: 09/805,768

(22) PCT Filed: Sep. 14, 1999

(86) PCT No.: PCT/FR99/02179

§ 371 (c)(1),
(2), (4) Date: Jul. 6, 2001

(87) PCT Pub. No.: WO00/15841

PCT Pub. Date: Mar. 23, 2000

(30) Foreign Application Priority Data

Sep. 16, 1998 (FR) ............................................. 98 11557

(51) Int. Cl.⁷ ........................ C12Q 1/68; G01N 33/574; C12P 19/34; C07H 21/02; C07H 21/04
(52) U.S. Cl. ........................ 435/6; 435/7.23; 435/91.1; 536/23.1; 536/24.3
(58) Field of Search ..................... 435/6, 7.5, 91.1, 435/7.23, 183, 91.2, 91.51; 436/94, 501, 63; 536/23.1, 24.3, 24.33, 24.32; 424/130.1, 140.1, 178.1, 179.1

(56) References Cited

U.S. PATENT DOCUMENTS 5,756,696 A 5/1998 Gray et al.

FOREIGN PATENT DOCUMENTS

EP 0 500 290 8/1992

OTHER PUBLICATIONS

Speicher, M., et al., Karyotyping human chromosomes by combinatorial multi–fluor FISH, Nature Genetics, vol. 12, Apr. 1996.*
Christina Voorter, et al, Loss of chromosome 11 and 11 P/Q Imbalances in Bladder Cancer Detected By . . . , Int. J. Cancer; vol. 65, pp. 301–307 (1996).*
Truong et al., Quantitative FISH by image cytometry for the detection of chromosome 1 imbalances in breast cancer: a novel approach analyzing chromosome rearrngements within interphase nuclei. Lab. Invest., 78, 1607–1613, Dec. 1998.*
Stratagene Catalog (1994), p. 121. Published by Stratagene Cloning Systems, 11011 North torrey Pines Road, La Jolla, CA 92037.*
Haugland, Handbook of fluorescent probes and research chemicals, Sixth Edition. published by Molecular Probes, Inc., 4849 Pitchford Avenue, Eugene, OR 97402–9165.*
R. I. Blough, et al., Cancer Genetics and Cytogenetics, vol. 94, No. 2, pp. 79–84, "Bicolor Fluorescent in Situ Hybridization on Nuclei From Formalin–Fixed, Paraffin–Embedded Testicular Germ Cell Tumors: Comparison With Standard Metaphase Analysis", Apr. 1997.
R. I. Blough, et al., Modern Pathology, vol. 11, No. 7, pp. 634–641, "Interphase Chromosome Painting of Paraffin–Embedded Tissue in the Differential Diagnosis of Possible Germ Cell Tumors", Jul. 1998.
D. C. Tkachuk, et al., Genetics Analysis Techniques and Applications, vol. 8, No. 2, pp. 67–74, "Clinical Applications in Situ Hybridization", Apr. 1, 1991.
P. J. Poddighe, et al., Cancer Research, vol. 52, No. 18, pp. 4929–4934, "Structural Chromosome 1 Aberrations in Transitional Cell Carcinoma of the Bladder: Interphase Cytogenetics Combining a Centromeric, Telomeric, and Library DNA Probe", Sep. 15, 1992.
K. Truong, et al., Laboratory Investigation, vol. 78, No. 12, pp. 1607–1613, "Quantitative FISH by Image Cytometry for the Detection of Chromosome 1 Imbalances in Breast Cancer: A Novel Approach Analyzing Chromosome Rearrangements Within Interphase Nuclei", Dec. 1998.

* cited by examiner

Primary Examiner—Ethan Whisenant
Assistant Examiner—Frank Lu
(74) Attorney, Agent, or Firm—Oblon, Spivak, McClelland, Maier & Neustadt, P.C.

(57) ABSTRACT

The invention concerns a method for detecting intrachromosome imbalance in interphase nuclei, characterized in that it consists in: (a) hybridizing in situ the chromosome suspected to be affected by said imbalance using two probes marked with different fluorochromes and specific of said chromosome long arm and short arm respectively; (b) measuring the intensity of the fluorescence emitted in said nuclei with different emission wavelengths corresponding to each of the two fluorochromes; (c) calculating the ratio (Ra) between the two measured values of fluorescence intensity; and (d) comparing the resulting ratio value with at least one reference value. The invention also concerns a kit for implementing said method and uses of said kit and said method, in particular for detecting cancer cells in a biological sample and for diagnosing cancer pathologies.

19 Claims, 1 Drawing Sheet

Figure 1A:
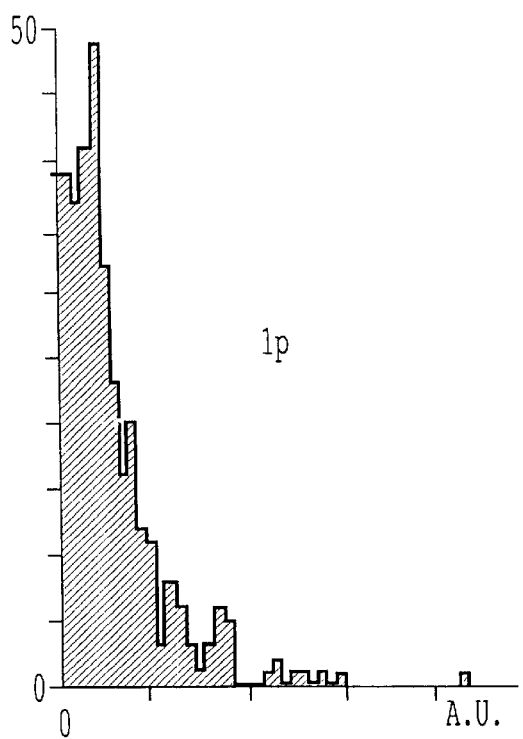

METHOD AND KIT FOR DETECTING INTRACHROMOSOME IMBALANCE IN INTERPHASE NUCLEI AND THEIR APPLICATIONS

The present invention relates to a method for detecting an intrachromosome imbalance in interphase cell nuclei, to an appropriate kit which makes it possible to carry out this method as well as to the applications of this method and of this kit, in particular for the detection of cancer cells in a biological sample and the diagnosis of cancer pathologies.

The cytogenetic study of tumor cells has shown the existence, in these cells, of numerous chromosome rearrangements consisting in particular of losses and gains of genetic material which can lead to the disappearance of chromosome arms or, on the contrary, to the presence of supernumerary chromosome arms and which thus result in modifications of the normal ratio between the number and/or the length of the long and short arms of certain chromosomes which will be designated hereinafter by the term intrachromosome imbalances.

Thus, for example, DUTRILLAUX et al. (*Cancer Genet. Cytogenet.*, 1990, 49, 203–217) have demonstrated, from 30 cases, the onset in breast cancers of multiple rearrangements affecting, at a particularly high frequently, chromosomes 1 and 16 and which manifest themselves mainly by a gain of the long arm of chromosome 1 and a loss of the long arm of chromosome 16, and, at a lower frequency, chromosomes 4, 6, 8, 9, 11, 13 and 17. Similarly, TESTA and SIEGFRIED (*Cancer Research*, 1992, 52, 2702s–2706s) have also shown, from 30 cases, the presence, in non-small cell lung cancers, of numerous rearrangements preferentially affecting chromosome 7 (mainly in the form of a polysomy 7 or of a gain of all or part of the short arm of this chromosome), but also chromosomes 1, 3, 6, 7, 11, 13, 15, 17 and 19.

Indeed, it is now well established that the process of cancerogenesis is a multistage event requiring successive genetic modifications whose accumulation over time will lead to cells with transforming potential which will be increasingly aggressive, leading to a clinically detectable and possibly metastasizing tumor. Accordingly, a precise definition of the cytogenetic parameters characteristic of tumorigenesis appears to constitute an essential step both in the establishment of the positive diagnosis and in that of the evolutive diagnosis of tumors, thus allowing the use of the most appropriate therapies.

Currently, cytogeneticists have available mainly two approaches in the investigation of the genome and of its abnormalities:

on the one hand, conventional cytogenetics, which makes it possible to have access to the detailed karyotype of a cell and to apprehend the abnormalities in the structure and in the number of all the chromosomes which it contains and which consists, after a period of culture in vitro of cells whose lifespan varies with the type of cells studied, in blocking these cells in the metaphase and in treating the chromosomes according to various methods allowing observation under an optical microscope of bands extending over a few megabases, and it is thus generally designated by the Anglo-Saxon name banding. After photographing, the chromosomes are paired and ordered according to their length, the position of the centromer and the topography of the bands, and this classification results in the establishment of the karyotype.

This approach, of which the major interest is to give an overall "image" of the genome, has a number of limitations.

The first relates to the fact that it requires prior culturing of the cells studied, so as to obtain a sufficient number of metaphase cells. However, it is now well established that, in the case of a polyclonal population, the carrying out of a cell culture is likely to introduce substantial bias into the results of a cytogenetic analysis, because of the fact that only the cells adapted to the culture conditions divide and give metaphases. Another limitation lies in the resolving power of conventional cytogenetics which makes it possible to apprehend only partially the often relatively complex chromosome rearrangements in solid tumors, which represent the majority of cancers. Finally, by virtue of its principle, this approach comes up against any possibility of an automated screening of complex and/or multiple chromosome abnormalities.

on the other hand, fluorescence in situ hybridization (FISH), which makes it possible to detect a chromosomal DNA sequence by means of a probe having a specific sequence which is homologous to that which is studied. Based on the complementarity existing between nucleotides (adenine-thymine, adenine-uridine, cytosine-guanine), it consists in hybridizing the target DNA with a probe labeled either directly or indirectly with a fluorochrome, and in using the fluorescence emitted by the latter as hybridization control.

Fluorescence in situ hybridization may be carried out on metaphase chromosomes, in which case it uses probes specific for a chromosome, for an arm, for a chromosomal region, or even for a given locus. The chromosomal abnormalities are revealed by visualization, under a microscope, of the fluorescent sites corresponding to the sites of the target DNA having hybridized with the probes. However, in routine pathological analysis, fluorescence in situ hybridization is carried out on interphase nuclei and it uses, in this case, probes specific for the centromer regions of the chromosomes. The chromosomal abnormalities are revealed by counting of the fluorescent spots either manually under a microscope or in an automated manner by means of an image cytometer, the number of spots being in all cases supposed to correspond to the number of copies of the chromosomes studied.

While the development of the FISH techniques has unquestionably improved the resolving power of cytogenetics (up to the order of a few kilobases), thus making it possible to better define the gains and losses of chromosomal material and the abnormalities in the structure of the chromosomes, these techniques as they currently exist, are not, however, completely satisfactory.

Indeed, as regards FISH on metaphase chromosomes a preliminary step of in vitro culture of the cells is essential, as in the case of conventional cytogenetics, in order to obtain a sufficient number of cells in the metaphase with the abovementioned disadvantages which that involves.

As regards FISH on interphase nuclei, while it has the advantage of avoiding the culturing step and, therefore, the potential selection of certain cells during this culture, it has the disadvantage that manual counting of these spots can only be carried out on a limited number of cells and is responsible for large errors when it is applied to a small population of abnormal cells (KIBBELAAR et al., *Cytometry*, 1993, 14, 716–724), while automated counting remains up until now highly imperfect, in spite of the efforts which have been made in order to improve the quality of the hybridization, the quality of the signals which it generates and the sensitivity of the cameras with which the image cytometers are equipped (TRUONG et al., *Anal. Cell Path*, 1997, 13, 137–146). What is more, it is the case that a number of chromosomal abnormalities do not affect the centromeric regions of the chromosomes, but their arms, and escape any possibility of detection by this technique.

The inventors therefore set themselves the objective of providing an appropriate method which allows the detection of an intrachromosome imbalance in the cells of a biological sample, and which is free, in general, from all the disadvantages of the methods of the prior state of the art.

More specifically, the inventors set themselves the objective of providing a method for detecting an intrachromosome imbalance which, while being sensitive, specific and reproducible so as to ensure the reliability of this detection, can:

on the one hand, be carried out on interphase cells so as to remove the need to subject beforehand the cells which have to be studied to an in vitro culture, on the other hand, be applied not only to a monoclonal cell population, but also to a polyclonal cell population so as to allow the detection of the possible presence, in this population, of abnormal cell clones even when these are in the minority, and in addition, be at least partially automated so as to make possible, for a reasonable cost, the treatment of a large quantity of biological samples while limiting the risks of errors in this treatment.

These aims are achieved according to the present invention by a method for detecting an intrachromosome imbalance in interphase cell nuclei, which is characterized in that it comprises:

(a) the in situ hybridization of the chromosome present in said nuclei and suspected of being affected by said imbalance using two probes labeled with two different fluorochromes, the first probe being specific for the long arm of this chromosome while the second probe is specific for the short arm of this same chromosome;

(b) measuring the intensity of the fluorescence emitted in said nuclei at the emission wavelength bands corresponding to each of the two fluorochromes;

(c) calculating the ratio between the two fluorescence intensity values thus measured; and (d) comparing the ratio value thus obtained with at least one reference value.

For the purposes of the present invention, the expression "intrachromosome imbalance" is understood to mean any modification of the normal ratio between the number and/or the length of the long and short arms of a chromosome resulting in a loss or in a gain of genetic material such as a deletion or, on the contrary, a duplication of all or part of a chromosome arm.

Moreover, for the sake of simplicity, in the text that follows, "target chromosome" refers to the chromosome suspected of being affected by an imbalance as defined above and for which it is sought to verify if the imbalance effectively exists.

In accordance with the invention, the two probes used for the in situ hybridization of the target chromosome consist of a set of nonrepeated probes covering all or part of the long arm or of the short arm of said chromosome.

Preferably, these probes consist of a set of probes covering the entire long arm or short arm of the target chromosome.

Such probes, which are commonly designated by the name chromosome paint, may be specially prepared for the purpose of being used in the method of detection in accordance with the invention.

Thus, for example, these probes may be prepared from cells known to have, at the level of the same chromosome as the target chromosome, an abnormality (deletion, isochromosome and the like) of the short arm or of the long arm such that this impaired chromosome substantially corresponds to one of the arms of the target chromosome, by sorting the chromosomes of these cells, for example by flow cytometry, so as to retain only the chromosomes suitable for use in the preparation of the probes, and then by subjecting these chromosomes to amplification, for example by the polymerase chain reaction technique PARM-PCR as described by MILAN et al. (*Mammalian Genome*, 1996, 7, 194–199), followed by labeling of the products resulting from this amplification with a fluorochrome.

As a variant, they may also be prepared from cells free of any chromosome abnormality, by laser or needle microdissection of the chromosome of these cells corresponding to the target chromosome so as to individualize the long arm and/or the short arm thereof, followed by amplification of the chromosome arm(s) thus obtained and then a labeling of the products resulting from this amplification with a fluorochrome, as described for example by GUAN et al. (*Hum. Molec. Genet.*, 1993, 2, 1117–1121).

It is of course also possible to resort, for the implementation of the method of detection in accordance with the invention, to ready-to-use commercial probes. Thus, for example, probes specific for the short and long arms of various human chromosomes and labeled with biotin are available from the company ALTECHNOLOGIES (USA).

Moreover, although the probes used for the in situ hybridization of the target chromosome can be probes directly coupled to a fluorochrome, these probes are preferably probes for indirect fluorescent labeling, the inventors having indeed observed that this type of labeling leads to particularly satisfactory results.

Thus, according to a preferred feature for implementing the method in accordance with the invention, the labeling of the probes used for the in situ hybridization of the target chromosome is carried out by coupling each of them to a hapten, and by an affinity reaction between this hapten and a ligand capable of binding specifically to said hapten and which is either conjugated with a fluorochrome, or which has been made fluorescent by reacting with a counterligand conjugated with a fluorochrome.

By way of examples of haptens which may be used for indirect labeling of the probes useful in the present invention, there may be mentioned in particular:

digoxigenin, dinitrophenol and 2-acetyl-aminofluoren, in which case the hapten/ligand affinity reaction is advantageously carried out using antibodies directed against these compounds and conjugated with a fluorochrome;

biotin, in which case the hapten/ligand affinity reaction is advantageously carried out using avidin conjugated with a fluorochrome, or using anti-biotin antibodies, and then antibodies directed against the latter and which are conjugated with a fluorochrome.

Preferably, one of the probes is coupled to digoxigenin while the other probe is coupled to biotin.

Whatever the type of labeling of the probes (direct or indirect), they are labeled, in accordance with the invention, with two different fluorochromes designed to allow, by the emission of light of two different colors, visualization of the long arms, on the one hand, and of the short arms, on the other hand, of the target chromosome having hybridized with the probes which are specific for them respectively.

These fluorochromes may equally well be chosen from the various fluorescent compounds used for the labeling of nucleic probes, such as fluorescein isothiocyanate (FITC), rhodamine derivatives such as rhodamine b isothiocyanate and sulforhodamine 101 sulfonate chloride (Texas red®), Cascade blue® or Bopidy® FL, provided, however, that care is taken to ensure that they have emission wavelength maxima situated in bands which do not overlap.

Thus, for example, in the case where one of the probes will be labeled with FITC whose emission wavelength maximum is situated at 543 nm, the other probe will be advantageously labeled with rhodamine b isothiocyanate whose emission wavelength maximum is situated at 590 nm or, better still, with Texas red® which has an emission wavelength maximum which is even further removed (604 nm) from that of FITC.

Preferably, one of the two fluorochromes is FITC, while the other is Texas red®.

According to yet anther preferred feature for implementing the method of detection in accordance with the invention, it comprises, furthermore, counter-staining of the nuclei designed to allow their visualization prior to the measurement of the intensity of the fluorescence emitted in these nuclei at the emission wavelength bands of the two fluorochromes coupled to the probes. This counterstaining is therefore performed before carrying out this measurement, using a fluorochrome different from those used for the labeling of the probes, such as 4',6-diamidino-2-phenylindole (DAPI) or 4',6-bis-2'-imidazolinyl 4H-5H (DIPI).

As indicated above, the method of detection comprises a step aimed at measuring the intensity of the fluorescence emitted in the nuclei at the emission wavelength bands corresponding to each of the two fluorochromes coupled to the probes.

Thus, for example, if the in situ hybridization of the target chromosome has been performed using a probe specific for the long arm of this chromosome labeled with FITC which emits a green light, and a probe specific for the short arm of this chromosome labeled with Texas red® which emits a red light, the intensity of the green fluorescence emitted by the nuclei and then the intensity of the red fluorescence emitted by these same nuclei are successively measured. Two fluorescence intensity values are obtained in this way which are dependent respectively on the number of long arms and the number of short arms of the target chromosome having hybridized with the probes which are specific for them.

In accordance with the invention, the ratio ($R_a$) between the two fluorescence intensity values thus measured is then calculated. Advantageously, this ratio is calculated by one and/or the other of the following methods:

a first method consisting in determining, for each fluorescence, the mean of the intensity values of this fluorescence as measured for all the nuclei analyzed, and in calculating the ratio between the two mean values thus obtained; and a second method consisting in calculating, for each nucleus analyzed, the ratio between the intensity values measured for each of the two fluorescences, and in determining the mean of the values of this ratio as obtained for all the nuclei analyzed.

The ratio ($R_a$) value thus obtained is then compared with at least one reference value.

Preferably, this reference value corresponds to the ratio ($R_t$) between the two fluorescence intensity values measured for the nuclei of control cells treated exactly under the same conditions as the nuclei analyzed.

Advantageously, the control cells are cells free of any chromosome abnormality, such as for example lymphocytes obtained from healthy subjects. Thus, a significant difference (that is to say in practice at least equal to 20%) between the ratio ($R_a$) and ($R_t$) values obtained for the nuclei analyzed and the nuclei of the control cells, respectively, indicates the existence, in at least a number of the nuclei analyzed, of the intrachromosome imbalance tested for.

It is, however, possible to also use, as control cells, cells affected by the intrachromosome imbalance which it is desired to detect, such as cells of a cell line known to constantly have this intrachromosome imbalance.

According to yet another preferred feature of the method of detection in accordance with the invention, it comprises, in addition, a step consisting in determining, for the nuclei analyzed, an imbalance index (I). Here again, this imbalance index may be advantageously established by one and/or the other of the following methods:

a first method consisting in calculating the ratio between the ratio ($R_a$) and ($R_t$) values obtained for all the nuclei analyzed and all the nuclei of the control cells, respectively, and a second method consisting in calculating, for each nucleus analyzed, the ratio between the ratio ($R_a$) and ($R_t$) values, and retaining, for example from a histogram representing the number of nuclei analyzed as a function of the $R_a/R_t$ ratio, the value of this ratio corresponding to the largest number of nuclei analyzed.

According to yet another preferred feature for implementing the method of detection in accordance with the invention, steps b), c), d) corresponding to the measurement of the fluorescence intensities, to the calculation of the ratio between these fluorescence intensities and to the comparison of the value of this ratio with a reference value, as well as the step for determining the imbalance index (I) for the nuclei analyzed, are carried out using an apparatus which comprises:

a source of light capable of providing light in three different wavelength bands, it being possible for said source to be either a polychromatic source provided with filters, or a source consisting of a plurality of monochromatic sources, means of measuring the intensity of the fluorescence emitted by fluorochromes in three different wavelength bands, and means of treating and analyzing the fluorescence intensities thus measured.

By way of example of apparatus which may be suitable for carrying out said steps, there may be mentioned the automated image analyzer marketed by the company BECTON DICKINSON IMAGE CYTOMETRY SYSTEMS under the registered trade mark DISCOVERY.

According to a preferred embodiment of the method of detection in accordance with the invention, the intrachromosome imbalance which it is sought to detect results from a duplication of the long arm of human chromosome 1 and/or from a deletion of the short arm of this chromosome.

The subject of the present invention is also a kit for implementing the method for detecting an intrachromosome imbalance in interphase intracellular nuclei as defined above, which is characterized in that it comprises:

an appropriate quantity of a first probe labeled with a first fluorochrome, said probe being specific for the long arm of the chromosome present in said nuclei and suspected of being affected by said imbalance, an appropriate quantity of a second probe labeled with a second fluorochrome, said probe being specific for the short arm of this same chromosome, one or more samples of a cell population free of any chromosome abnormality and, optionally, one or more samples of a cell population consisting partly or completely of cells having the imbalance which it is desired to detect.

According to a first advantageous feature of the kit in accordance with the invention, the control cell samples are provided in the form of platings on slides ready to be subjected to an in situ hybridization.

According to another advantageous feature of the kit in accordance with the invention, the probes are coupled to a hapten, and the kit comprises, for each probe, an appropriate quantity of a ligand directed specifically against this hapten and which is conjugated with a fluorochrome or capable of being made fluorescent by a reaction with a counterligand conjugated with a fluorochrome, in which case the kit contains, furthermore, an appropriate quantity of said counterligand.

According to yet another advantageous feature of this kit, it comprises in addition:

an appropriate quantity of one or more reagents for fixing the cells; and/or an appropriate quantity of a third fluorochrome for allowing counterstaining of the cell nuclei; and/or an appropriate quantity of reagents (RNase, pepsine and the like) and buffer solutions (hybridization buffers, rinsing buffers and the like) for allowing in situ hybridization of the chromosome with the probes.

The subject of the present invention is also the application of the method for detecting an intrachromosome imbalance in interphase cell nuclei and of the kit for allowing implementation of this method as defined above, to the detection of cancer cells in a biological sample such as a fine needle aspiration biopsy, serum effusion (pleural, peritoneal and the like), tumorectomy or bronchial aspiration.

Indeed, the method of detection in accordance with the invention is of especial interest in the field of human cancerology and more particularly for establishing positive diagnosis and/or evolutive diagnosis of cancer pathologies in which a number of chromosome rearrangements is recurrently observed which result in imbalances in the normal ratio between the number and/or the length of the long and short arms of certain chromosomes, such as the depletion of the long arm of chromosomes 1 and 8, the deletion of the short arm of chromosomes 1 and 3 or the deletion of the long arm of chromosome 6.

This method may also find application in fields other than cancerology, and in particular in establishing positive diagnosis of inherent or acquired human pathologies linked to chromosome abnormality such as, for example, cat's cry syndrome which is characterized by a deletion of part of the short arm of chromosome 5.

Figure 1B:
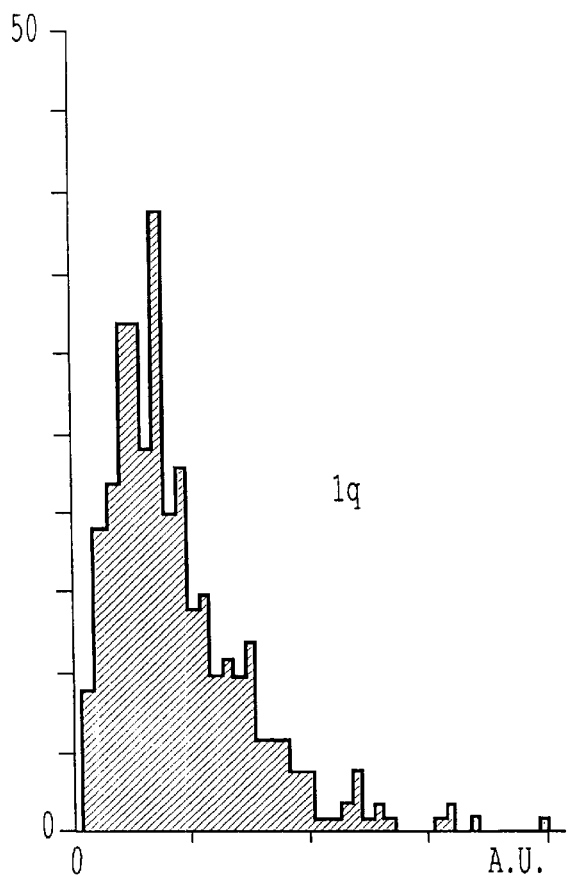

In addition to the preceding features, the invention further comprises other features which will emerge from the following description which refers to an example of implementation and application of the method of detection in accordance with the invention as well as to the appended FIG. 1 which illustrates, in the form of histograms, the distributions of the number of nuclei as a function of the fluorescence intensities as measured for the long arm (1q) (FIG. 1B), on the one hand, and the short arm (1p) (FIG. 1A), on the other hand, of chromosome 1 by implementing said method on cells obtained from a tumor sample.

It should be understood, however, that this example is given solely by way of illustration of the subject of the invention and does not constitute in any manner a limitation thereto.

EXAMPLE

Detection of an Imbalance between the Long and Short Arms of Chromosome 1 in Breast Cancer Cells The method of detection in accordance with the invention and the benefit of its use for diagnostic purposes were validated by a series of experiments aimed at applying this method to the search for the imbalance between the long arm (hereinafter "arm 1q") and the short arm (hereinafter "arm 1p") of chromosome 1 frequently observed in the case of breast cancers, and at comparing the results obtained with those observed using two techniques conventionally used in cytogenetics, namely the R-banding technique, on the one hand, and the fluorescence in situ hybridization technique (FISH) on metaphase chromosomes, on the other hand.

1) Biological Materials

The experiments were carried out on 2 types of breast cancer cell:

on the one hand, tumor cells belonging to 3 cell lines: ZR 75, BT 20 and H 466 and obtained respectively from the strains deposited at the ATCC (AMERICAN TYPE CULTURE COLLECTION) under the Nos. CRL-1500, HTB-19 and HTB-171; and on the other hand, tumor cells obtained from biological samples collected from 16 patients aged between 33 and 73, and corresponding to 13 tumors and 6 fine needle aspiration biopsies, 2 patients having been the subject of both a fine needle aspiration biopsy and then a tumorectomy, and 1 patient having been the subject of 2 tumorectomies (right breast and left breast).

Among these biological samples, 3 were found to correspond to stage I tumors, 4 to stage IIA tumors, 8 to stage IB tumors, 1 to a stage IIIA tumor and 1 to a stage IIIB tumor, based on the grouping by stage by the AMERICAN JOINT COMMITTEE OF CANCER (AJCC). Moreover, histology made it possible to show that this involved in 10 cases infiltrating ductal carcinomas, in 3 cases infiltrating lobular carcinomas, and in 3 other cases an undifferentiated carcinoma, a colloid carcinoma and an intraductal carcinoma. According to the SCARFF-BLOOM-RICHARDSON (SBR) grading method, 3 tumors were grade II while 5 were grade III.

2) Preparation of Slides of Tumor Cells

The cell lines were cultured under standard conditions. They were fixed either with Carnoy's fluid, or with 0.5% paraformaldehyde in PBS buffer with, in the latter case, post-fixing with ethanol at 70%, and then spread on slides.

The tumors and half of the fine needle aspiration biopsies were cultured for a short period (72 hours) as described by MULERIS et al. (*Genes, Chromosomes & Cancer,* 1994, 10, 160–170). The cells obtained from these cultures were then fixed with Carnoy's fluid and spread on slides.

The other fine needle aspiration biopsies, after dilution (10-fold) in dissociating medium No. C 1419 (SIGMA), were fixed with 0.5% para-formaldehyde in PBS buffer, post-fixed with ethanol at 70% and then spread on slides by centrifugation by means of a Cytospin® 3 centrifuge (SHANDON).

3) Preparation of Slides of Control Cells

Slides of control cells were prepared by spreading lymphocyte cells free of any chromosome abnormality, after fixing these cells, for a portion of these slides, with Carnoy's fluid and, for the other portion, with 0.5% paraformaldehyde in PBS buffer, followed, in the latter case, by post-fixing with ethanol at 70%.

4) Preparation of the Probes

For the production of probes specific for arm 1q and for arm 1p, chromosome suspensions of the cell lines H 466 and DU 145 (strain available from ATCC under the No. HTB-81), characterized respectively by an iso(1q) chromosome rearrangement and by a del(1)(q10-qter) chromosome rearrangement, were prepared according to the technique described by VAN DEN ENGH et al. (*Cytometry,* 1984, 5, 108–117).

A total of 300 chromosomes corresponding either to iso(1q), or to del(1)(q10-qter) were sorted by flow cytometry. These chromosomes were then amplified by the polymerase chain reaction technique PARM-PCR using primers (GAG)7 and labeled according to the protocols described by MILAN et al. (*Mammalian Genome,* 1996, 7, 194–199), using as markers, digoxigenin-11-dUTP (BOEHRINGER MANNHEIM) for the chromosomes intended to serve as probes for the arm 1q and biotin-11-dUTP (SIGMA) for the chromosomes intended to serve as probes for the arm 1p.

5) In situ Hybridization

The in situ hybridization was conducted by making a few minor modifications to the protocol described by TRUONG et al., (*Anal. Cell Path.,* 1997, 13, 137–146). In practice, after treatment with RNase (100 µg/ml, SIGMA) at 37° C. for one hour, followed by two rinsings in 2×SSC buffer and rinsing in PBS buffer, the slides of tumor cells and of control cells were incubated at 37° C. for 10 minutes, in the presence of pepsin (SIGMA) at a concentration of 4 µg/ml in 0.01 M HCl. They were then rinsed twice in PBS buffer for 5 minutes and at room temperature, post-fixed in Carnoy's fluid and air-dried.

The DNA of the chromosomes designed to serve as probes was denatured at 70° C. for 10 minutes in a conventional hybridization buffer. The target DNA, that is to say the DNA of the slides of tumor cells and of control cells, was, for its part, denatured at 70° C. for 3 minutes in 2×SSC buffer comprising 70% of formamide (FLUKA), pH 7. The slides were then rinsed in 2×SSC buffer and then dehydrated using increasing concentrations of ethanol and air-dried.

The hybridization was performed at 37° C. overnight and then the sample slides were subjected to post-hybridization rinses in 2×SSC buffer, for 5 minutes at 72° C.

6) Measurement of the Fluorescence Intensities and Determination of the Ratio between the Values of These Intensities To allow visualization of the 1q and 1p arms of chromosomes 1 of the tumor cells and of the control cells which have hybridized with the probes, the slides were incubated:

on the one hand, with anti-digoxigenin antibodies labeled with FITC (BOEHRINGER MANNHEIM) which emits fluoresence which is green in color, and on the other hand, with mouse anti-biotin antibodies, and then anti-mouse immunoglobulin anti-bodies labeled with Texas Red® (MOLECULAR PROBES), the latter emitting fluoresence which is red in color.

The slides were then counterstained with DAPI (1 µg/ml, MOLECULAR PROBES), and then mounted in p-phenylenediamine.

The measurement of the green and red fluorescence intensities corresponding to the arms 1q and 1p, respectively, of chromosomes 1 which have hybridized with the probes was carried out using an automated image analyzer DISCOVERY® (BECTON DICKINSON IMAGE CYTOMETRY SYSTEMS) comprising:

a light source consisting of a mercury vapor lamp with a power of 100 W (OSRAM), an AUTOPLAN® microscope (LEITZ) provided with an oil immersion lens and at magnification 40 (numerical aperture: 1.3), a black and white CCD camera XILLIX® 1400 provided with a shutter which makes it possible to vary the integration time for exposure to light between 30 msec and 10 sec, a suitable image acquisition card for digitizing the signal delivered by the camera, and connected to this card, a microcomputer comprising a central processing unit marketed by the company INTEL under the reference 486 and provided with the image processing software DISCOVERY®.

For each slide, the counterstain DAPI was, in a first instance, excited at the wavelength of 330 nm so as to visualize the zones of the image formed by the optical system on the sensor of the camera, which are occupied by the nuclei and to define the optimum adjustment of this image. The green and red fluorescence intensities emitted in these nuclei were then successively measured using, as relevant zones of these fluorescences, the zones of the image which have been detected as corresponding to zones occupied by the nuclei.

The optimum integration time was determined for each of the fluorescences relative to a slide of control cells and was then used for all the slides of tumor cells which have to be analyzed.

Per slide, 500 to 700 nuclei were counted and only one measurement of the fluorescences was carried out. The artifacts, the image zones which were not recognized as corresponding to zones occupied by a nucleus and the nuclei free of any green and red fluorescence were eliminated by an operator. As the quantity of nuclei thus excluded could in some cases reach 20% depending on the quality of hybridization, analyzable results were able to be obtained for a minimum of 400 nuclei for each slide.

The image analyzing software DISCOVERY® made it possible to obtain an analysis of these results in the form of histograms. By way of illustration, FIG. 1 shows the histograms obtained for a slide corresponding to one of the biological samples (sample 94T) and representing the number of nuclei as a function of the fluorescence intensities as measured for the arm 1q, on the one hand, and the arm 1p, on the other hand.

In the case of the cell lines ZR 75, BT 20 and H 466, the ratio ($R_a$) between the fluorescence intensities corresponding to the arm 1q and to the arm 1p, respectively, was calculated by two different methods:

a first method (hereinafter "method 1") consisting in determining, for each slide, using the image analyzing software DISCOVERY®, the mean of the green fluorescence intensities (arm 1q) and the mean of the red fluorescence intensities (arm 1p) emitted in the nuclei and in calculating the ratio between the mean values thus obtained; and a second method (hereinafter "method 2") consisting in determining the ratio between the green fluorescence intensity (arm 1q) and the red fluorescence intensity (arm 1p) emitted in each nucleus, in establishing, using the EXCEL® software marketed by the company MICROSOFT, the histogram representing the number of nuclei as a function of the value of the ratios thus obtained for an entire slide and in calculating, from this histogram, the mean of these ratios.

In the case of biological samples (tumors and fine needle aspiration biopsies), only the second method of calculation was used since the two methods of calculation were found to lead to comparable results as will be demonstrated below, this second method makes it possible to obtain results more rapidly.

In all cases, the existence of an imbalance between the arms 1q and 1p in the tumor cells analyzed was assessed by characterizing these cells by an imbalance index ($I_i$) calculated as follows:

$$I_i = \frac{R_a}{R_t}$$

$R_t$ representing between the fluorescence intensities corresponding respectively to the arm 1q and to the arm 1p obtained for the slides of lymphocytic cells treated and analyzed exactly under the same conditions.

7) Measurement of the Background Noise

The importance of the background noise was assessed by analyzing slides of tumor cells which have not been subjected to any hybridization and by comparing the results obtained with those observed for slides of tumor cells which have been the subject of an in situ hybridization under the conditions described above. It was thus possible to verify that the background noise represents on average less than 20% of the specific signals and that as a result of these, it does not interfere significantly with the fluorescence measurements.

8) Control Cytogenetic Analyses

Every time it was possible to obtain, from the cell lines ZR 75, BT 20 and H 466, and the biological samples, slides comprising a sufficient number of metaphase cell, these slides were also subjected to two cytogenetic analyses intended to serve as controls: one conventional cytogenetic analysis by the R-banding technique, on the one hand, and a molecular cytogenetic analysis by the FISH technique on metaphase chromosomes, on the other hand.

The conventional cytogenetic analysis was carried out in accordance with the methods described by DUTRILLAUX et COUTURIER (*La Pratique de l'Analyse Chromosomique*, 1981, MASSON, 12, 7–87) while the molecular cytogenetic analysis, for its part, was carried out according to the protocol described by MULERIS et al. (*Oncogene*, 1994, 9, 2717–2722).

These analyses made it possible to observe a number of rearrangements affecting chromosomes 1 of the analyzed cells—which are not reported here—, and to establish for each cell population, from these observations, an imbalance index ($I_m$) calculated as follows:

$$I_m = \frac{\text{Quantity of copies of arm 1q (green color)}}{\text{Quantity of copies of arm 1p (red color)}}$$

9) Results a) Tumor Cells of the Cell Lines

The cell lines ZR 75, BT 20 and H 466 represent populations of tumor cells which have the double advantage of being very homogeneous since they are derived from the same clone, and of providing, insofar as they are maintained in a permanent culture, a sufficient number of metaphase cells to allow systematic checking of the results obtained with the method of detection which is the subject of the invention by the R-banding and FISH techniques on metaphase chromosomes.

That is the reason why the inventors chose to use these cell lines to verify the reliability of the method of detection in accordance with the invention and to test the influence, on the results obtained, of the mode of fixing the cells which have to be analyzed as well as the method of calculating the ratio between the fluorescence intensities corresponding to the arm 1q and to the arm 1p, respectively.

Table 1 below presents:

on the one hand, the imbalance indices ($I_i$) between the arms 1q and 1p as obtained for the 3 cell lines ZR 75, BT 20 and H 466 by the method of detection in accordance with the invention, this being as a function of the type of fixative [Carnoy's fluid or paraformaldehyde (PBA)] used during the preparation of the slides, and as a function of the method [method 1 or method 2] used for calculating the ratio between the fluorescence intensities corresponding to the arm 1q and to the arm 1p, respectively, and on the other hand, the imbalance indices ($I_m$) between the arms 1q and 1p as obtained for these same cell lines by the R-banding and FISH techniques on metaphase nuclei.

TABLE I

| Cell lines | | $I_i$ | | $I_m$ | |
| --- | --- | --- | --- | --- | --- |
| | Fixing | Method 1 | Method 2 | R-banding | FISH |
| ZR 75 | CARNOY | 2.2 | 1.8 | 2 | 2 |
| | CARNOY | 2.3 | 2.2 | | |
| | PFA | 1.8 | 2.2 | | |
| | PFA | 2 | 2.2 | | |
| BT 20 | CARNOY | 1 | 1 | 1.5 | 1 |
| | CARNOY | 1 | 1.1 | | |
| | PFA | 1 | 1 | | |
| | PFA | 0.9 | 1.1 | | |
| H 466 | CARNOY | 1.5 | 2 | 2 | 2 |
| | CARNOY | 1.8 | 1.9 | | |

These results show that the imbalance indices between the arms 1q and 1p obtained by the method of detection in accordance with the invention are in full agreement with those determined by the R-banding and the FISH techniques on metaphase chromosomes, this being independently of the mode of fixing the cells analyzed and the method of calculating the ratio between the fluorescence intensities corresponding to the arm 1q and to the arm 1p, respectively.

b) Tumor Cells in the Biological Samples

Table 2 below presents:

on the one hand, the imbalance indices ($I_i$) between the arms 1q and 1p as obtained for the 13 tumors and the 6 fine needle aspiration biopsies by the method in accordance with the invention, and on the other hand, the imbalance indices ($I_m$) between the arms 1q and 1p as determined for these biological samples by the R-banding and FISH techniques on metaphase chromosomes, when it was possible to use these two techniques.

TABLE 2

| Biological samples | $I_i$ | $I_m$ | |
| --- | --- | --- | --- |
| | | R-banding | FISH |
| 84T | 3.3 | 3 | 3 |
| 86T | 2.1 | 1.5 | — |
| 94T | 1.8 | 2 | 2 |
| 152T | 1.4 | 1.3 | — |
| 221T | 2.2 | 2 | 2 |
| 230T | 1 | 1.3 | — |
| 1007T$^R$ | 1.3 | 1.5 | 1.5 |
| 1007T$^L$ | 1.5 | 1.5 | — |
| 1015T | 1.6 | 1.5 | 1.5 |
| 1024T | 1 | 1 | — |
| 1040T | 1.5 | 1.5 | 1.5 |
| 1F | 1 | — | — |
| 2F | 1.7 | — | — |
| 252T | 1 | 1.3 | — |
| 252F | 1.1 | — | — |
| 253F | 1 | 1.5 | — |

TABLE 2-continued

| Biological samples | $I_i$ | $I_m$ | |
|---|---|---|---|
| | | R-banding | FISH |
| 256F | 1.5 | >1 | — |
| 1039T | 1.3 | 1–1.5 | — |
| 1039F | 1.3 | — | — |

T = tumor; $T^R$ = tumor of the right breast; $T^L$ = tumor of the left breast; F = fine needle aspiration biopsy These results demonstrate an excellent correlation (r=0.89 determined by the linear regression method using the STAT-VIEW® software marketed by the company MICROSOFT) between the imbalance indices obtained by the method of detection in accordance with the invention and those determined by the R-banding technique except in 4 cases (86T, 230 T, 252T and 253F) in which the latter technique appears not to have made it possible to detect all the arms 1q and 1p present because of the complexity of the karyotypes.

As is evident from the above, the invention is not at all limited to these embodiments, implementations and applications which have just been described more explicitly; it encompasses, on the contrary, all the variants which may occur to the specialist in this field, without departing from the framework or the scope of the present invention.

What is claimed is:

1. A method for detecting an intrachromosome imbalance in one or more interphase cell nuclei, comprising:

(a) an in situ hybridization of a chromosome present in said nuclei and suspected of being affected by said imbalance using two probes labeled with two different fluorochromes, the first probe being specific for long arms of said chromosome and the second probe is specific for short arms of the same chromosome;

(b) measuring the fluorescence intensity values emitted in said nuclei at the emission wavelengths corresponding to each of the two fluorochromes;

(c) calculating a ratio between the two fluorescence intensity values measured in step (b) ($R_a$); and (d) comparing $R_a$ thus obtained in step (c) with at least one reference value, wherein said reference value is the ratio ($R_t$), wherein $R_t$ is the ratio of two fluorescent intensity values obtained from the nuclei of control cells treated under the same conditions described in steps (a) and (b), (e) wherein a significant difference of $R_a$ and $R_t$ is indicative of the intrachromosomal imbalance.

2. The method of claim 1, wherein the probes used for the in situ hybridization of the chromosome consist of a set of nonrepeated probes covering all or part of the long arm or all or part of the short arm of said chromosome.

3. The method of claim 1, wherein the probes used for the in situ hybridization of the chromosome consist of a set of nonrepeated probes covering the entire long arm or entire short arm of the target chromosome.

4. The method of claim 1,
    wherein each of said probes is coupled to a different hapten,
    wherein each of said haptens binds to a different ligand, and
    wherein each ligand is labeled with a different fluorochrome, or each ligand is recognized by a counterligand conjugated with a different fluorochrome.

5. The method of claim 4, wherein one of the probes is coupled to digoxigenin and the other is coupled to biotin.

6. The method of claim 1, wherein the two fluorochromes are selected from the group consisting of fluorescein isothiocyanate (FITC) and a rhodamine derivative.

7. The method of claim 6, wherein at least one of the two fluorochromes is selected from the group consisting of rhodamine b isothiocyanate, sulforhodamine 101 sulfonate chloride, Cascade blue® and Bopidy® FL.

8. The method of claim 1, wherein one of the two fluorochromes is fluorescein isothiocyanate and the second fluorochrome is sulforhodamine 101 sulfonate chloride.

9. The method of claim 1, further comprising counterstaining the nuclei with a fluorochrome different from the fluorochromes used for labeling the probes.

10. The method of claim 1, wherein $R_a$ in step (c) is calculated using the mean fluorescent intensity value of each probe for all the nuclei analyzed.

11. The method of claim 1, wherein $R_a$ in step (c) is calculated using the mean fluorescent intensity value of each probe for each nucleus.

12. The method of claim 1, wherein the control cells are free of any chromosomal abnormality.

13. The method of claim 1, further comprising determining an imbalance index (I).

14. The method of claim 13, wherein I is determined by calculating the ratio between $R_a$ and $R_t$ wherein $R_a$ and $R_t$ are calculated using the mean fluorescent intensity value of each probe for all the nuclei analyzed and all the nuclei of the control cells, respectively.

15. The method of claim 13, wherein (I) is determined by calculating the ratio between $R_a$ and $R_t$ wherein $R_a$ and $R_t$ are calculated using the mean fluorescent intensity value of each probe for each nucleus and each nucleus of the control cells, respectively.

16. The method of claim 13, wherein steps b), c), d) as well as a step for determining the imbalance index (I) the nuclei analyzed, are carried out using an apparatus comprising:

a source of light providing light in three different wavelengths, wherein said source is either a polychromatic source provided with filters or a source consisting of a plurality of monochromatic sources, means for measuring the intensity of the fluorescence emitted by fluorochromes in three different wavelengths, and means for treating and analyzing the fluorescence intensities measured by the means for measuring the intensity of the fluorescence.

17. The method of claim 1,
    wherein said intrachromosome imbalance results from a duplication of the long arm of human chromosome 1 or from a deletion of the short arm of this chromosome, or both.

18. A method for detecting cancer cells in a biological sample comprising the method of claim 1.

19. A method for diagnosing cancer pathology in a human comprising the method of claim 1.

* * * * *